(12) United States Patent
Simon

(10) Patent No.: US 7,520,849 B1
(45) Date of Patent: Apr. 21, 2009

(54) PULSED ELECTROMAGNETIC FIELD METHOD OF TREATING SOFT TISSUE WOUNDS

(75) Inventor: Bruce J. Simon, Mountain Lakes, NJ (US)

(73) Assignee: EBI, LP, Parsippany, NJ (US)

( * ) Notice: Subject to any disclaimer, the term of this patent is extended or adjusted under 35 U.S.C. 154(b) by 1121 days.

(21) Appl. No.: 10/945,291

(22) Filed: Sep. 20, 2004

(51) Int. Cl.
*A61N 1/00* (2006.01)

(52) U.S. Cl. .......................................... 600/14

(58) Field of Classification Search ................. 600/9–15
See application file for complete search history.

(56) References Cited

U.S. PATENT DOCUMENTS

| | | | |
|---|---|---|---|
| 4,019,510 A | 4/1977 | Ellis | |
| 4,105,017 A | 8/1978 | Ryaby et al. | |
| 4,266,533 A | 5/1981 | Ryaby et al. | |
| 4,315,503 A | 2/1982 | Ryaby et al. | |
| 4,683,873 A | 8/1987 | Cadossi et al. | |
| 4,738,250 A | 4/1988 | Fulkerson et al. | |
| 4,846,181 A | 7/1989 | Miller | |
| 4,895,154 A | 1/1990 | Bartelt et al. | |

(Continued)

FOREIGN PATENT DOCUMENTS

WO  WO 2004/011631  2/2004

OTHER PUBLICATIONS

N. Guzelsu et al., "Effect of Electromagnetic Stimulation with Different Waveforms on Cultured Chick Tendon Fibroblasts," *Bioelectromagnetics*, vol. 15, 1994, pp. 115-131.

(Continued)

*Primary Examiner*—John P Lacyk
(74) *Attorney, Agent, or Firm*—William F. Bahret

(57) ABSTRACT

A pulsed electromagnetic field method of treating a soft tissue wound, wherein, in one embodiment, a patient in need of treatment for a soft tissue wound is administered a pulsed electromagnetic field (PEMF) having repetitive pulse bursts less than approximately 30 ms in duration, with a pulse burst repetition rate greater than approximately 5 Hz, the pulse bursts generated with a drive signal including pulses each having a first-polarity portion with a pulse width less than 1 ms and a second-polarity portion with a shorter pulse width, the electromagnetic field having a maximum amplitude less than approximately 4 mT and rising to its maximum amplitude during the first-polarity portion. According to another aspect of the invention, a soft tissue wound is treated by administering a pulsed electromagnetic field having substantially unipolar magnetic field pulses generated with a drive signal including a series of pulses each having a first-polarity portion with a pulse width less than 1 ms and a second-polarity portion with a longer pulse width, the electromagnetic field having a maximum amplitude less than 4 mT and rising to its maximum amplitude during the first-polarity portion.

42 Claims, 4 Drawing Sheets

U.S. PATENT DOCUMENTS

| | | | |
|---|---|---|---|
| 4,919,138 | A | 4/1990 | Nordenstroom |
| 5,107,835 | A | 4/1992 | Thomas |
| 5,158,081 | A | 10/1992 | McWhorter et al. |
| 5,195,940 | A | 3/1993 | Baylink |
| 5,338,296 | A | 8/1994 | Abbott et al. |
| 5,366,435 | A | 11/1994 | Jacobson |
| 5,370,680 | A | 12/1994 | Proctor |
| 5,387,176 | A | 2/1995 | Markoll |
| 5,395,398 | A | 3/1995 | Rogozinski |
| 5,433,735 | A | 7/1995 | Zanakis et al. |
| 5,458,558 | A | 10/1995 | Liboff et al. |
| 5,518,496 | A | 5/1996 | McLeod et al. |
| 5,968,527 | A | 10/1999 | Litovitz |
| 6,099,459 | A | 8/2000 | Jacobson |
| 6,132,362 | A | 10/2000 | Tepper et al. |
| 6,200,259 | B1 | 3/2001 | March |
| 6,261,221 | B1 | 7/2001 | Tepper et al. |
| 6,334,069 | B1 | 12/2001 | George et al. |
| 6,443,883 | B1 | 9/2002 | Ostrow et al. |
| 6,561,968 | B1 | 5/2003 | Dissing et al. |
| 2003/0130707 | A1 | 7/2003 | Gan et al. |
| 2005/0049640 | A1 | 3/2005 | Gurtner et al. |
| 2005/0084962 | A1 | 4/2005 | Simon |
| 2005/0271738 | A1 | 12/2005 | Simon |

OTHER PUBLICATIONS

M. J. Stiller, et al., "A Portable Pulsed Electromagnetic Field (PEMF) Device to Enhance Healing of Recalcitrant Venous Ulcers: A Double-Blind Placebo-Controlled Clinical Trial," *Journal of Investigative Dermatology*, 1992, pp. 147-154.

C. E. Campbell et al., "Effect of Electrical Stimulation on Wound Healing: A Review," in Ferdinando Bersani (ed), *Electricity and Magnetism in Biology and Medicine*, Kluwer Academic/Plenum Publishers, 1999, pp. 865-869.

L. C. Kloth et al., "Promotion of Wound Healing with Electrical Stimulation," *Advances in Wound Care*, vol. 9, No. 5, Sep./Oct. 1996, pp. 42-45.

L.C. Kloth et al., "Effect of Pulsed Radio Frequency Stimulation on Wound Healing: A Double-Blind Pilot Clinical Study," *Electricity and Magnetism in Biology and Medicine*, Kluwer Academic/Plenum Publishers, 1999, pp. 857-878.

Arthur A. Pilla, "State of the Art in Electromagnetic Therapeutics: Soft Tissue Applications," *Electricity and Magnetism in Biology and Medicine*, Kluwer Academic/Plenum Publishers, 1999, pp. 871-874.

J.G. Fleischli et al., "Electrical Stimulation in Wound Healing," *The Journal of Foot & Ankle Surgery*, vol. 36, No. 6, 1997, pp. 457-461.

M. Akai et al., "Effect of Electrical Stimulation on Musculoskeletal Systems; A Meta-Analysis of Controlled Clinical Trials," *Bioelectromagnetics*, vol. 23, 2002, pp. 132-143.

S. E. Gardner et al., "Effect of Electrical Stimulation on Chronic Wound Healing: A Meta-Analysis," *Wound Repair and Regeneration*, vol. 7, No. 6, Nov.-Dec. 1999, pp. 495-503.

Richard Nuccitelli, "A Role for Endogenous Electric Fields in Wound Healing," *Current Topics in Developmental Biology*, vol. 58, 2003, pp. 1-26 (proof copy).

R. Goodman, et al., "Exposure of Human Cells to Low-Frequency Electromagnetic Fields Results in Quantitative Changes in Transcripts," *Biochimica et Biophysica Acta*, vol. 1009, 1989, pp. 216-220.

J. Kantor et al., "Expected Healing Rates for Chronic Wounds," Medscape Pulmonary Medicine [online], vol. 12, No. 6, © 2000 [retrieved Mar. 26, 2001]. Retrieved from the Internet: http://www.medscape.com/HMP/wounds/2000/v12.n06/21206.02kant/pnt-w1206.02.kant.html.

D. J. Margolis et al., "Healing of Diabetic Neuropathic Foot Ulcers Receiving Standard Treatment A Meta-Analysis," *Diabetes Care*, vol. 22, No. 5, May 1999, pp. 692-695.

Martin C. Robson, M.D., "The Role of Growth Factors in the Healing of Chronic Wounds," *Wound Repair and Regeneration*, vol. 5, No. 1, Jan.-Mar. 1997, pp. 12-17.

K. Fukushima et al., "Studies on Galvanotaxis of Leukocytes," *Medical Journal of Osaka University*, vol. 4, No. 2-3, Nov. 1953, pp. 195-208.

C. A. Erickson et al., "Embryonic Fibroblast Motility and Orientation Can Be Influenced by Physiological Electric Fields," *The Journal of Cell Biology*, vol. 98, Jan. 1984, pp. 296-307.

N. Orida et al., "Directional Protrusive Pseudopodial Activity and Motility in Macrophages Induced by Extracellular Electric Fields," *Cell Motility*, vol. 2, 1982, pp. 243-255.

T. M. Mohr et al., "Effect of High Voltage Stimulation on Edema Reduction in the Rat Hind Limb," *Physical Therapy*, vol. 67, No. 11, Nov. 19867, pp. 1703-1707.

M. Brown, et al., "Polarity Effects on Wound Healing Using Electric Stimulation in Rabbits," *Arch. Phys. Med. Rehabil.*, vol. 70, Aug. 1989, pp. 624-627.

M. Brown et al., "High-Voltage Galvanic Stimulation on Wound Healing in Guinea Pigs: Longer-Term Effects," *Arch. Phys. Med. Rehabil.*, vol. 76, Dec. 1995, pp. 1134-1137.

Brian V. Reed, "Effect of High Voltage Pulsed Electrical Stimulation on Microvascular Permeability to Plasma Proteins," *Physical Therapy*, vol. 68, No. 4, Apr. 1988, pp. 491-495.

V. Falanga et al., "Electrical Stimulation Increases the Expression of Fibroblast Receptors for Transforming Growth Factor-Beta," *J Invest Dermatol*, vol. 88, No. 4, Apr. 1987, Abstracts for the 1987 Annual Meeting of the Society for Investigative Dermatology, Inc., San Diego, California, May 4-6, 1987 (pp. 474 and 488).

C. B. Kincaid et al., "Inhibition of Bacterial Growth In Vitro Following Stimulation with High Voltage, Monophasic Pulsed Current," *Physical Therapy*, vol. 69, No. 8, Aug. 1989, pp. 651-655.

L. J. Laatsch et al., "In Vitro Effects of Two Silver Electrodes on Select Wound Pathogens," *Journal of Clinical Electrophysiology*, vol. 7, No. 1, pp. 10-15, 1995.

G. J. Bourguignon, "Electric Stimulation of Protein and DNA Synthesis in Human Fibroblasts," *FASEB Journal*, vol. 1, 1987, pp. 398-402.

N. I. Cruz et al., "Accelerated Healing of Full-Thickness Burns by the Use of High-Voltage Pulsed Galvanic Stimulation in the Pig," *Annals of Plastic Surgery*, vol. 23, Jul. 1989, pp. 49-55.

M. Brown et al., "Effects of High Voltage Stimulation on Cutaneous Wound Healing in Rabbits," *Physical Therapy*, vol. 67, No. 5, May 1987, pp. 662-667.

D. G. Lorich et al., "Biochemical Pathway Mediating the Response of Bone Cells to Capacitive Coupling," *Clinical Orthopaedics and Related Research*, No. 350, May 1998, pp. 246-256.

H. Zhuang et al., "Electrical Stimulation Induces the Level of TGF-$\beta 1$ mRNA in Osteoblastic Cells by a Mechanism Involving Calcium/Calmodulin Pathway," *Biochemical and Biophysical Research Communications*, vol. 237, No. 2, 1997, pp. 225-229.

C. G. Greenough, "The Effects of Pulsed Electromagnetic Fields on Blood Vessel Growth in the Rabbit Ear Chamber," *Journal of Orthopaedic Research*, vol. 10, No. 2, 1992, pp. 256-262.

G. Yen-Patton, et al., "Endothelial Cell Response to Pulsed Electromagnetic Fields: Stimulation of Growth Rate and Angiogenesis in Vitro," *Journal of Cellular Physiology*, vol. 134, 1988, pp. 37-46.

T. Bodamyali et al., Pulsed Electromagnetic Fields Simultaneously Induce Osteogenesis and Upregulate Transcription of Bone Morphogenetic Proteins 2 and 4 in Rat Osteoblasts in Vitro, *Biochemical and Biophysical Research Communications*, vol. 250, No. 2, 1998, pp. 458-461.

H. Guerkov et al., "Pulsed Electromagnetic Fields Increase Growth Factor Release by Nonunion Cells," *Clinical Orthopaedics and Related Research*, No. 384, Mar. 2001, pp. 265-279.

R. Aaron et al., "Stimulation of Growth Factor Synthesis by Electric and Electromagnetic Fields," *Clin Orthop*, No. 419, Feb. 2004, pp. 30-37.

O. Tepper et al., "Electromagnetic Fields Increase in Vitro and in Vivo Angiogenesis Through Endothelial Release of FGF-2," *The FASEB Journal express article 10.1096/fj.03-0847fje*, http://www.fasebj.org/cgi/reprint/03-0847fjev1, published online Jun. 18, 2004, 16 pages.

D. Ornitz et al., "Fibroblast Growth Factors," *Genome Biology*, vol. 2, No. 3, 2001, pp. 1-12.

A. Medina et al., "Pathophysiology of Chronic Nonhealing Wounds," *Journal of Burn Care and Rehabilitation*, vol. 26, No. 4, 2005, pp. 306-319.

T. Mustoe, et al., "Chronic Wound Pathogenesis and Current Treatment Strategies: A Unifying Hypothesis," *Plastic and Reconstructive Surgery*, vol. 117, No. 7S, Jun. Supplement 2006, pp. 35S-41S.

D. Ciombor et al., "Modification of Osteoarthritis by Pulsed Electromagnetic Field—A Morphological Study," *OsteoArthritis and Cartilage*, vol. 11, No. 6, 2003, pp. 455-462.

C. H. Lohmann et al., "Pulsed Electromagnetic Fields Affect Phenotype and Connexin 43 Protein Expression in MLO-Y4 Osteocyte-like Cells and ROS 17/2.8 Osteoblast-like Cells," *Journal of Orthopaedic Research*, vol. 21, 2003, pp. 326-334.

C. H. Lohmann et al., "Pulsed Electromagnetic Field Stimulation of MG63 Osteoblast-like Cells Affects Differentiation and Local Factor Production," *Journal of Orthopaedic Research*, vol. 18, 2000, pp. 637-646.

M. Ieran et al., "Effect of Low Frequency Pulsing Electromagnetic Fields on Skin Ulcers of Venous Origin in Humans: A Double-Blind Study," *J Ortho Res*, vol. 8, No. 2, 1990, pp. 276-282 (Abstract).

M. Itoh et al., "Accelerated Wound Healing of Pressure Ulcers by Pulsed High Peak Power Electromagnetic Energy (Diapulse)," *Decubitus*, vol. 4, No. 1, 1991, pp. 29-34 (Abstract).

C. A. Salzberg et al., "The Effects of Non-Thermal Pulsed Electromagnetic Energy on Wound Healing of Pressure Ulcers in Spinal Cord-Injured Patients: A Randomized, Double-Blind Study," *Ostomy Wound Manage*, vol. 41, No. 3, 1995, pp. 42-44 (Abstract).

US 7,520,849 B1

PULSED ELECTROMAGNETIC FIELD METHOD OF TREATING SOFT TISSUE WOUNDS

BACKGROUND OF THE INVENTION

This invention relates to wound treatment, and more particularly to methods of treating soft tissue wounds with the aid of electrical stimulation.

Chronic wounds, such as pressure ulcers, venous ulcers and diabetic ulcers, are significant public health concerns. Within the United States, the annual incidence of such chronic wounds is greater than 7 million. Further, the incidence of these chronic wounds increases as much as 14% per year. This is particularly true for diabetic ulcers, which afflict about 15% of the 16 million diabetics in the United States. Each year, approximately 85,000 lower-extremity amputations are performed as a result of treatment failure of diabetic ulcers. Such chronic wounds occur in approximately 31% of diabetic patients and take up to 20 weeks to heal. The incidences of venous and pressure ulcers within the United States are estimated to be 1.3 million and 3 million, respectively, with an annual growth rate of about 6%.

Wound healing involves a series of interrelated events including coagulation, inflammation, deposition and differentiation of extracellular matrix, fibroplasia, epithelialization, contraction and remodeling. There are slight differences in the healing process depending on the type of wound. For example, the healing of a chronic pressure ulcer mainly involves deposition of extracellular matrix and contraction. However, a partial-thickness burn wound primarily heals through epithelialization. On the other hand, the healing of diabetic ulcers can be further complicated by other diabetic issues such as neuropathy, poor circulation and decreased response to infection.

Presently, chronic wound patients are faced with a lack of effective treatment options and a high cost of care. Currently available treatment methods for the type of wounds described above include various types of dressings, debridement/irrigation, pressure relieving devices, ultrasound, whirlpool/pulsed lavage, ultraviolet, pulsed frequency radiation, low-energy laser, hyperbaric or topically applied oxygen, cytokine growth factors, antibiotics and topical and systemic drugs. Research has also been centered on developing surgical glues, sealants and dressing, artificial skin and growth factors such as transforming growth factors (TGF-$\beta$), fibroblast growth factor (aFGF and bFGF), platelet-derived growth factor (PDGF), epidermal growth factor (EGF), insulin-like growth factors (IGF-I and IGF-II) and interleukins (IL-1 and IL-2). Other research has focused on reducing the pressure on the soft tissue by designing a variety of wheelchair cushions, pads, shoes, mattresses and beds to distribute the pressure more evenly over the body. Unfortunately, even with the best available wound care procedures, chronic wounds tend to heal very slowly, not heal at all, or even worsen.

An alternative approach to wound healing is the implementation of electrical stimulation. The rationale for using electrical stimulation is based on the fact that the human body has endogenous bioelectric systems that promote wound healing. However, when the body's endogenous bioelectric system is inadequate, external electrical stimulation can be used to supplement the natural bioelectric currents or electric fields for enabling or enhancing wound healing.

There are several disadvantages associated with prior art methods of electrical stimulation for wound healing. One disadvantage is that many prior art methods require placement of one or perhaps two electrodes directly on the soft tissue wound. Such placement increases the probability of bacterial contamination, thereby complicating wound healing and further, acid or base build-up on the electrodes can adversely effect healing in the wound area. Other prior art devices and methods are inconvenient or difficult to employ as a result of their bulk or complexity. For example, several prior art devices require the implementation of several electrodes, whereby one electrode is applied directly over the wound area or immersed in a saline solution containing the body part with the wound and at least one other electrode is positioned on the patient as far away from the wound as possible. This makes extended treatment periods uncomfortable for the patient, as well as prohibiting free travel of the patient.

Several studies describe the use of direct current, pulsed electromagnetic fields, pulsed current, and radio frequency stimulation for the repair of ulcers, but the results of these studies have not been encouraging. In principle, electrical stimulation could accelerate the healing of ulcers and other soft tissue wounds, and numerous possibilities have existed for stimulation signal types and waveforms which might be considered for such purposes, but, despite years of research in this area, a need remains for a more effective signal for treatment of soft tissue wounds.

Thus, it is desirable to provide an improved electrical stimulation method for promoting wound healing of soft tissue wounds, such as venous, diabetic and pressure ulcers. The method should treat the wound area without actual contact with the wound to reduce the probability of bacterial infection. Further, the method should be simple and inexpensive while effectively treating soft tissue wounds.

SUMMARY OF THE INVENTION

The present invention provides an improved method of treating soft tissue wounds with the aid of electrical stimulation. More specifically, with a new treatment method according to one aspect of the present invention, a patient in need of treatment for a soft tissue wound is administered a pulsed electromagnetic field (PEMF) having repetitive pulse bursts less than approximately 30 ms in duration, with a pulse burst repetition rate greater than approximately 5 Hz, the pulse bursts generated with a drive signal including pulses each having a first-polarity portion with a pulse width less than 1 ms and a second-polarity portion with a shorter pulse width, the electromagnetic field having a maximum amplitude less than approximately 4 mT and rising to its maximum amplitude during the first-polarity portion.

According to another aspect of the present invention, a soft tissue wound is treated by administering to a patient in need of such treatment a pulsed electromagnetic field having substantially unipolar magnetic field pulses generated with a drive signal including a series of pulses each having a first-polarity portion with a pulse width less than 1 ms and a second-polarity portion with a longer pulse width, the electromagnetic field having a maximum amplitude less than 4 mT and rising to its maximum amplitude during the first-polarity portion.

The objects and advantages of the present invention will be more apparent upon reading the following detailed description in conjunction with the accompanying drawings.

DESCRIPTION OF PREFERRED EMBODIMENTS

Figure 1:
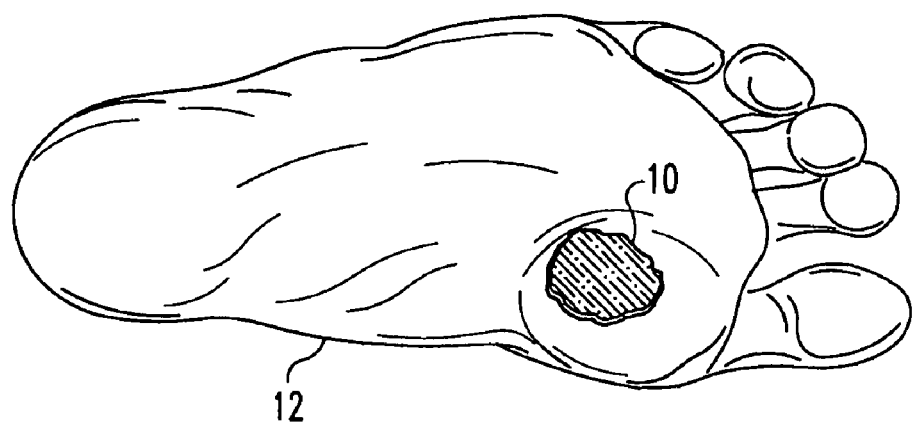
FIG. 1 is a bottom view of a human foot with a soft tissue wound.

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device and such further applications of the principles of the invention as illustrated therein being contemplated as would normally occur to one skilled in the art to which the invention relates.

Figure 2:
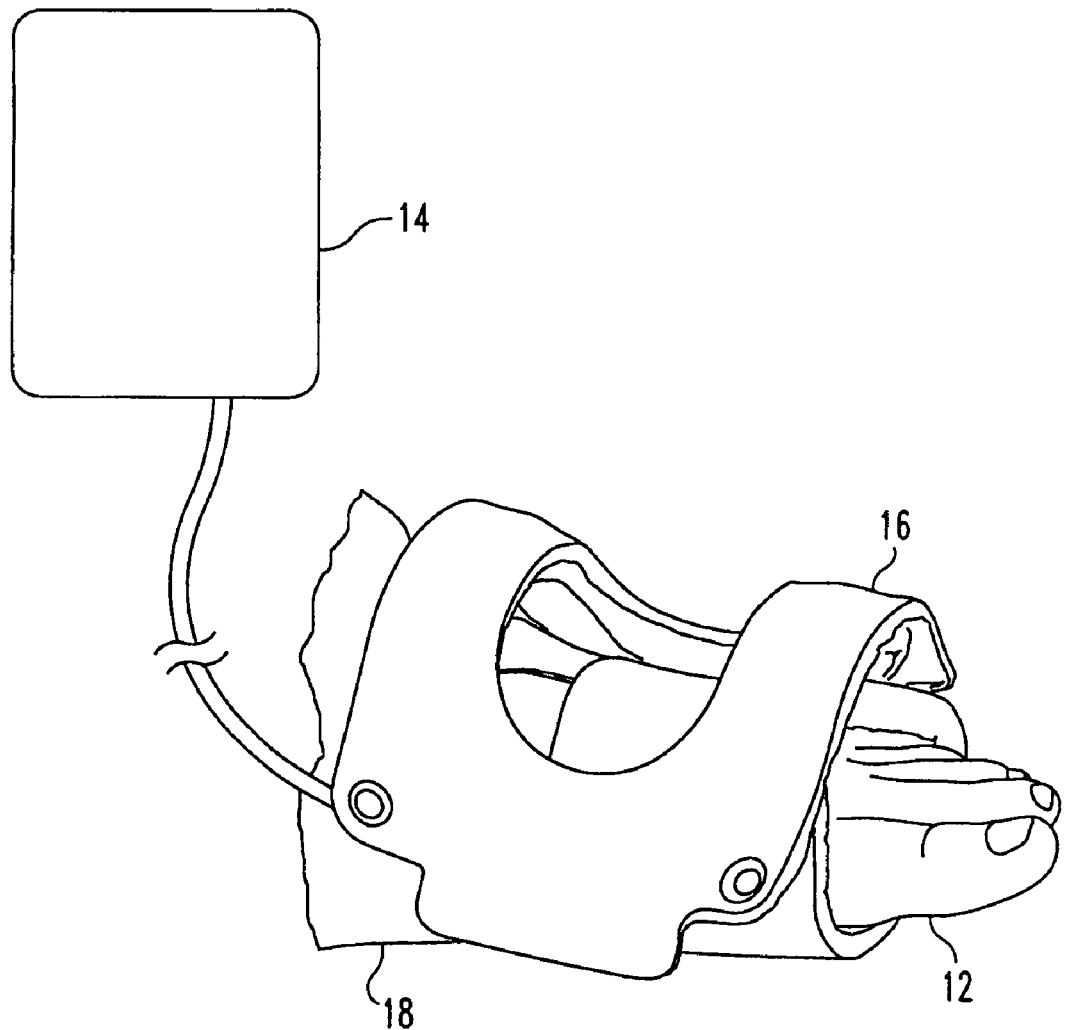
FIG. 2 is a perspective view of a PEMF signal generator and an associated treatment coil placed over the foot shown in FIG. 1 for treatment of the soft tissue wound.

Referring to FIGS. 1 and 2, a subject suffering from a soft tissue wound 10 on the foot 12 is treated with a pulsed electromagnetic field (PEMF) generated with a signal generator 14 and a treatment coil 16 which, in the example illustrated, is placed over the foot in a position to expose the wound on the ball of the foot to a pulsed electromagnetic field having the signal characteristics described herein. The soft tissue wound may be an ulcer, e.g., a venous ulcer, pressure ulcer, or diabetic ulcer, and it may be located on a body extremity such as shown in FIG. 1 or elsewhere on a patient's body, such as on the torso or head. The coil may be a saddle-shaped coil which at least partially surrounds the ulcer and the surrounding tissue, and it may be held in place with a bandage or tape, for example, or, as shown in FIG. 2, may be held in place with Velcro® or other suitable fastener around or as part of a padded boot 18 which may be provided for support and to cover conventional dressing on the wound. The coil is connected via a cable in a conventional manner to the signal generator, which may be held against the patient's body, e.g., on the thigh or on the waist in any suitable manner.

Figure 3A:
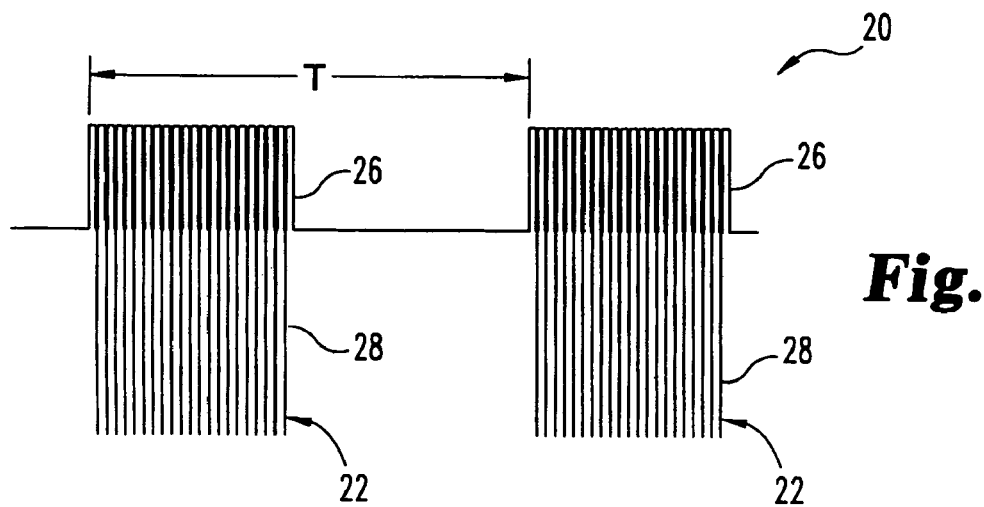
FIG. 3 illustrates a PEMF signal for use in soft tissue wound treatment according to one embodiment of the present invention, FIGS. 3A and 3B illustrating an electrical drive signal and FIG. 3C illustrating a corresponding magnetic field waveform.
Figure 3B:
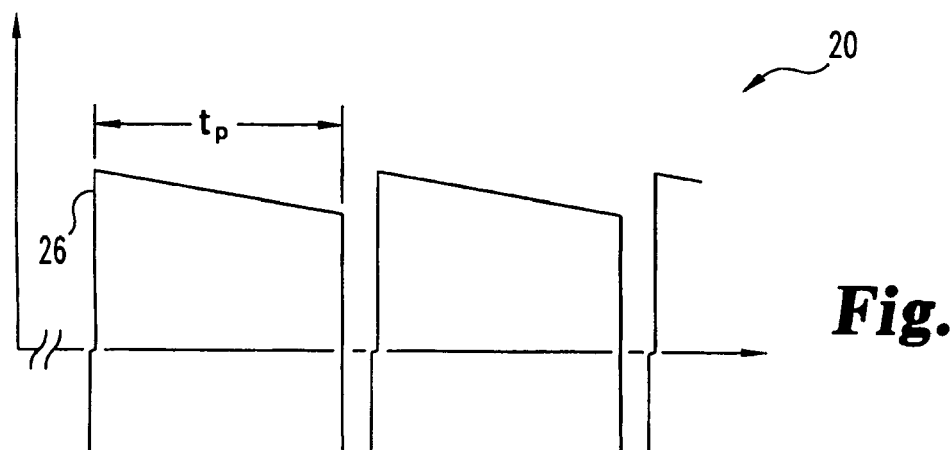
Figure 3C:
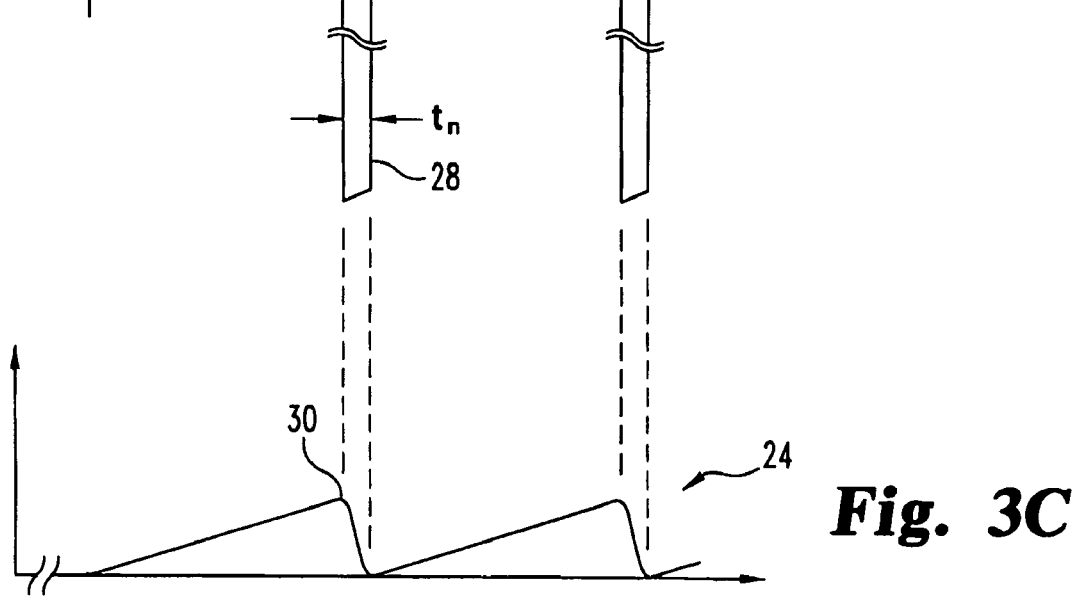

In one embodiment of the invention, the coil is supplied with an electrical drive signal such as signal 20 shown in FIGS. 3A and 3B. The signal comprises pulse bursts 22 less than approximately 30 milliseconds (ms) in duration, repeated at a rate greater than approximately 5 pulse bursts per second, i.e., a burst repetition rate greater than approximately 5 Hz. It will be appreciated that the resulting magnetic field 24 shown in FIG. 3C has these same characteristics. The drive signal has a positive portion 26 which is longer in duration than the negative portion 28. For example, the pulse width of the positive portion ($t_p$) is less than 1 ms, and advantageously in the range of 100-300 microseconds (μs), whereas the pulse width of the negative portion ($t_n$) is preferably less than 100 μs. A more preferred range for the positive pulse width is 200-250 μs, and the negative pulse width is more preferably in the range of 5-40 μs. The pulse bursts preferably have a duration of 2.5-5 ms and a repetition rate of 5-20 Hz.

One suitable example pulse train signal has positive and negative pulse widths of 200 μs and 24 μs, respectively, with total spacing between positive portions of 28 μs, and has 4.5-5 ms bursts repeated at 15 Hz. The peak magnetic flux density (B) 30 is preferably in the range of 0.9-1.8 milliTesla (mT) (9-18 Gauss), and more preferably approximately 1.5 mT, which is reached during the positive portion of the signal as shown in the drawing. The magnetic field is substantially unipolar in that it has little or no negative portion. Such a signal may be generated with, for example, an EBI Model 2001 Bone Healing System signal generator coupled to an EBI FLX® 1-2 or 2-2 flexible treatment coil. It will be understood that "positive" and "negative" are relative terms. Other signals which may be suitable for particular applications are described in U.S. Pat. Nos. 4,105,017, 4,266,533 and 4,315,503 to Ryaby et al., which patents are hereby incorporated by reference. A PEMF signal as described above is preferably applied for 2-12 hours per day, and more preferably approximately 8 hours per day as adjunctive therapy until the wound is healed.

Figure 4A:
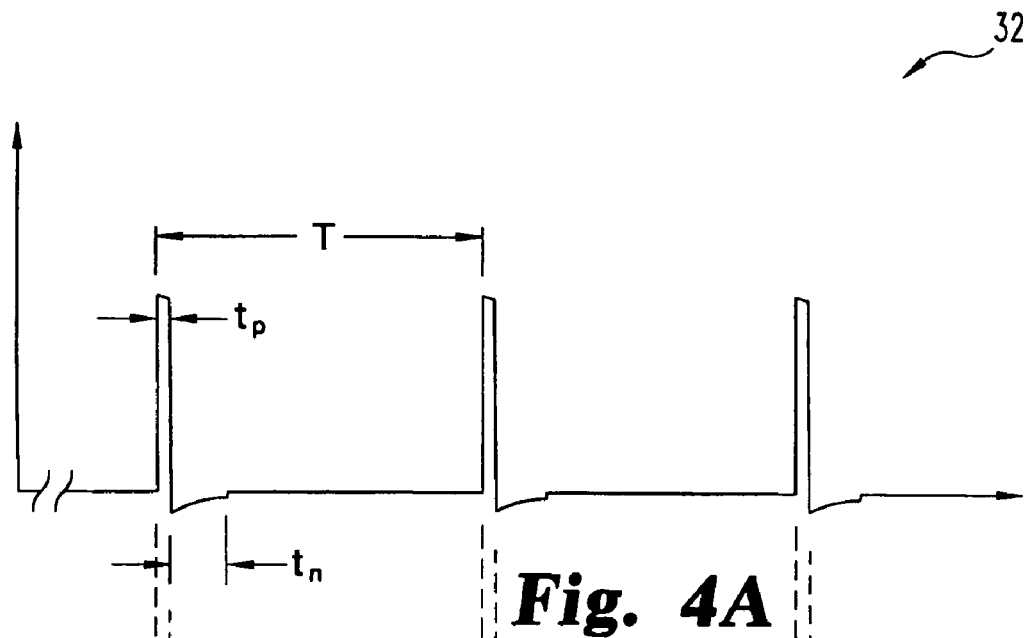
FIG. 4 illustrates a PEMF signal for use in soft tissue wound treatment according to another embodiment of the present invention, FIG. 4A illustrating an electrical drive signal and FIG. 4B illustrating a corresponding magnetic field waveform.
Figure 4B:
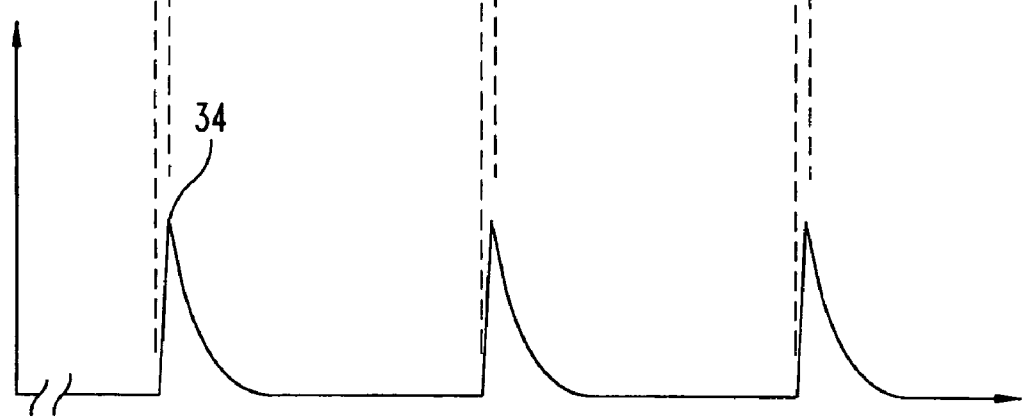

In another embodiment of the invention, a PEMF signal having repetitive single pulses such as shown in FIGS. 4A and 4B is administered to a patient with an identified soft tissue wound which is desired to be treated. Each pulse in the drive signal 32 has a positive pulse width ($t_p$) less than 1 ms, and advantageously in the range of 300-500 μs. The negative portion ($t_n$) of the drive signal is longer in duration than the positive portion, preferably longer than 3 ms. The pulse repetition rate (1/T) is preferably greater than 30 Hz, and more preferably in the range of 65-80 Hz.

One suitable example signal with repetitive single pulses has positive and negative pulse widths of approximately 380 μs and 4.5 ms, respectively, and a repetition rate of approximately 72 Hz. The magnetic field is substantially unipolar as shown, and the peak magnetic flux density (B) 34 is preferably in the range of 1.7-3.4 mT, and more preferably approximately 2.4 mT. Such a signal may be generated with, for example, an EBI Model 1020S Bone Healing System signal generator coupled to an EBI FLX® 2-S, 3-S or 4-S flexible treatment coil.

The PEMF signals described above have been shown to accelerate wound healing. For example, a 15 Hz pulse train as described above, with 4.5 ms pulse bursts, was administered to wild type and diabetic mice. 5 mm circular wounds were created on the dorsum of db/db and wild type C57BL6 mice, splinted open and covered with an occlusive dressing. Mice were exposed to PEMF (4.5 ms pulse/15 hz) for 8 hrs/day for 14 days. Gross closure was assessed with digital analysis of area changes over time. Histological examination assessed granulation and epithelial gap, cell proliferation (BrdU), and endothelial cell density (CD31). Human umbilical vein endothelial cells (HUVECs) were incubated in the presence or absence of PEMF for 8 hrs and growth factors were measured in culture supernatants by ELISA.

The diabetic mice exposed to PEMF had accelerated wound closure at day 7 (wound area as % of original, PEMF: 60% vs. control: 78%, p<0.05) and day 14 (PEMF: 21% vs. control: 55%, p<0.05). Because wild-type mice heal twice as fast as diabetics, wounds were analyzed on days 4 and 8. Accelerated closure was evident in PEMF wild-type mice at day 4 (PEMF: 15% vs. 42%, p<0.05) and day 8 (8% vs. 28%, p<0.05). In wound bed histological sections, granulation and cell proliferation were both increased in PEMF treated diabetic mice (day 7: 52±8 vs. 31±5 cells per high power field (200×)). Immunohistochemical analysis revealed significantly higher CD31 density in diabetic wounds exposed to PEMF at day 7 (PEMF: 28±4 vs. control 17±4 vessels per high power field) and day 14 (PEMF: 32±6 vs. control: 21±5). Increases were also seen in wild-type C57BL6 mice at day 7 (PEMF: 41±7 vs. control: 28±6) and day 14 (PEMF: 48±5 vs. control: 40±5). HUVECs cultured in PEMF exhibited 5-fold higher levels of fibroblast growth factor 2 (FGF-2) compared to controls after as little as 30 min stimulation (20.50 pg/ml±6.75 vs. 4.25 pg/ml±0.75) with no change in vascular endothelial growth factor (VEGF).

Figure 5:
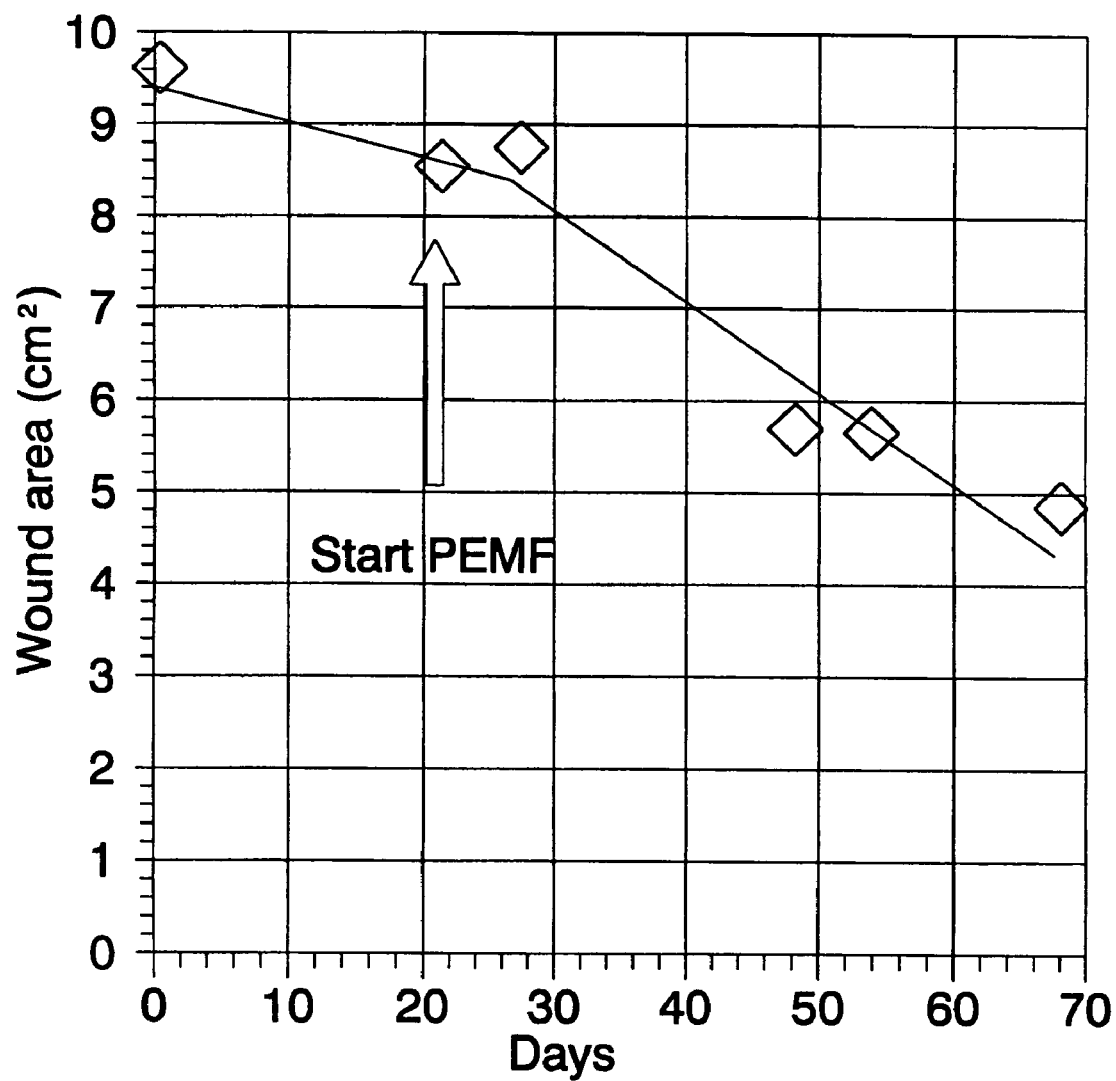
FIG. 5 is a graph of data obtained in a wound healing study using a signal of the type shown in FIG. 4.

A study using the 72 Hz repetitive single pulse PEMF signal described above was conducted in which human patients having ulcers on the medial surface of the foot were treated for 8-10 hours per day for up to 70 days. The results are as shown in FIG. 5, in which it is indicated that the PEMF treatment was started after 20 days of monitoring the extent of natural healing in terms of wound area measurements. The patients received the same standard of care before and after PEMF administration.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:

1. A pulsed electromagnetic field method of treating a soft tissue wound, comprising administering to a patient in need of such treatment a pulsed electromagnetic field having substantially unipolar magnetic field pulses generated with a drive signal including a series of pulses each having a first-polarity portion with a pulse width less than 1 ms and a second-polarity portion with a longer pulse width, said electromagnetic field having a maximum amplitude less than 4 mT and rising to said maximum amplitude during said first-polarity portion.

2. The method of claim 1, wherein said pulses are repetitive single pulses with a repetition rate greater than 30 Hz.

3. The method of claim 2, wherein said pulse width of said first-polarity portion is in the range of 300-500 μs, and said pulse width of said second-polarity portion is greater than 3 ms.

4. The method of claim 3, wherein said repetition rate is in the range of approximately 65-80 Hz.

5. The method of claim 4, wherein said maximum amplitude of said electromagnetic field is in the range of approximately 2-3 mT.

6. A pulsed electromagnetic field method of treating a soft tissue wound, comprising:
   identifying a soft tissue wound on a subject;
   indicating the use of a pulsed electromagnetic field for treatment of the identified soft tissue wound on the subject in need of such treatment, the indicated electromagnetic field characterized by substantially unipolar magnetic field pulses generated with a drive signal including a series of pulses each having a first-polarity portion with a pulse width less than 1 ms and a second-polarity portion with a longer pulse width, said electromagnetic field having a maximum amplitude less than 4 mT and rising to said maximum amplitude during said first-polarity portion.

7. The method of claim 6, wherein said pulses are repetitive single pulses with a repetition rate greater than 30 Hz.

8. The method of claim 7, wherein said pulse width of said first-polarity portion is in the range of 300-500 μs, and said pulse width of said second-polarity portion is greater than 3 ms.

9. The method of claim 8, wherein said repetition rate is in the range of approximately 65-80 Hz.

10. The method of claim 9, wherein said maximum amplitude of said electromagnetic field is in the range of approximately 2-3 mT.

11. A pulsed electromagnetic field method of treating a soft tissue wound, comprising:
    placing a treatment coil on the body of a subject at the site of an identified soft tissue wound; and
    applying a pulsed electromagnetic field to said soft tissue wound via said treatment coil for treatment of the identified soft tissue wound, said electromagnetic field characterized by substantially unipolar magnetic field pulses generated with a drive signal including a series of pulses each having a first-polarity portion with a pulse width less than 1 ms and a second-polarity portion with a longer pulse width, said electromagnetic field having a maximum amplitude less than 4 mT and rising to said maximum amplitude during said first-polarity portion.

12. The method of claim 11, wherein said pulses are repetitive single pulses with a repetition rate greater than 30 Hz.

13. The method of claim 12, wherein said pulse width of said first-polarity portion is in the range of 300-500 μs, and said pulse width of said second-polarity portion is greater than 3 ms.

14. The method of claim 13, wherein said repetition rate is in the range of approximately 65-80 Hz.

15. The method of claim 14, wherein said maximum amplitude of said electromagnetic field is in the range of approximately 2-3 mT.

16. A pulsed electromagnetic field method of treating a soft tissue wound, comprising administering to a patient in need of such treatment a pulsed electromagnetic field having repetitive pulse bursts less than approximately 30 ms in duration, with a pulse burst repetition rate greater than approximately 5 Hz, said pulse bursts generated with a drive signal including pulses each having a first-polarity portion with a pulse width less than 1 ms and a second-polarity portion with a shorter pulse width, said electromagnetic field having a maximum amplitude less than approximately 4 mT and rising to said maximum amplitude during said first-polarity portion.

17. The method of claim 16, wherein said pulse width of said first-polarity portion is in the range of approximately 100-300 μs.

18. The method of claim 17, wherein said pulse burst repetition rate is in the range of approximately 5-20 Hz.

19. The method of claim 18, wherein said pulse burst duration is in the range of approximately 2.5-5 ms.

20. The method of claim 19, wherein said maximum amplitude of said electromagnetic field is in the range of approximately 1-3 mT.

21. The method of claim 16, wherein said pulse width of said first-polarity portion is in the range of approximately 200-250 μs, and said pulse width of said second-polarity portion is approximately 25 μs.

22. The method of claim 21, wherein said pulse burst repetition rate is approximately 15 Hz.

23. The method of claim 22, wherein said pulse burst duration is approximately 5 ms.

24. The method of claim 23, wherein said maximum amplitude of said electromagnetic field is approximately 1.5 mT.

25. A pulsed electromagnetic field method of treating a soft tissue wound, comprising:
    identifying a soft tissue wound on a subject;
    indicating the use of a pulsed electromagnetic field for treatment of the identified soft tissue wound on the subject in need of such treatment, the indicated electromagnetic field characterized by repetitive pulse bursts less than approximately 30 ms in duration, with a pulse burst repetition rate greater than approximately 5 Hz, said pulse bursts generated with a drive signal including pulses each having a first-polarity portion with a pulse width less than 1 ms and a second-polarity portion with a shorter pulse width, said electromagnetic field having a maximum amplitude less than approximately 4 mT and rising to said maximum amplitude during said first-polarity portion.

26. The method of claim 25, wherein said pulse width of said first-polarity portion is in the range of approximately 100-300 μs.

27. The method of claim 26, wherein said pulse burst repetition rate is in the range of approximately 5-20 Hz.

28. The method of claim 27, wherein said pulse burst duration is in the range of approximately 2.5-5 ms.

29. The method of claim 28, wherein said maximum amplitude of said electromagnetic field is in the range of approximately 1-3 mT.

30. The method of claim 25, wherein said pulse width of said first-polarity portion is in the range of approximately 200-250 μs, and said pulse width of said second-polarity portion is approximately 25 μs.

31. The method of claim 30, wherein said pulse burst repetition rate is approximately 15 Hz.

32. The method of claim 31, wherein said pulse burst duration is approximately 5 ms.

33. The method of claim 32, wherein said maximum amplitude of said electromagnetic field is approximately 1.5 mT.

34. A pulsed electromagnetic field method of treating a soft tissue wound, comprising:
    placing a treatment coil on the body of a subject at the site of an identified soft tissue wound; and
    applying a pulsed electromagnetic field to said soft tissue wound via said treatment coil for treatment of the identified soft tissue wound, said electromagnetic field characterized by repetitive pulse bursts less than approximately 30 ms in duration, with a pulse burst repetition rate greater than approximately 5 Hz, said pulse bursts generated with a drive signal including pulses each having a first-polarity portion with a pulse width less than 1 ms and a second-polarity portion with a shorter pulse width, said electromagnetic field having a maximum amplitude less than approximately 4 mT and rising to said maximum amplitude during said first-polarity portion.

35. The method of claim 34, wherein said pulse width of said first-polarity portion is in the range of approximately 100-300 μs.

36. The method of claim 35, wherein said pulse burst repetition rate is in the range of approximately 5-20 Hz.

37. The method of claim 36, wherein said pulse burst duration is in the range of approximately 2.5-5 ms.

38. The method of claim 37, wherein said maximum amplitude of said electromagnetic field is in the range of approximately 1-3 mT.

39. The method of claim 34, wherein said pulse width of said first-polarity portion is in the range of approximately 200-250 μs, and said pulse width of said second-polarity portion is approximately 25 μs.

40. The method of claim 39, wherein said pulse burst repetition rate is approximately 15 Hz.

41. The method of claim 40, wherein said pulse burst duration is approximately 5 ms.

42. The method of claim 41, wherein said maximum amplitude of said electromagnetic field is approximately 1.5 mT.

* * * * *